United States Patent
Nakahara

(10) Patent No.: US 10,117,724 B2
(45) Date of Patent: Nov. 6, 2018

(54) BEARING UNIT FOR AIR TURBINE

(71) Applicant: NSK LTD., Tokyo (JP)

(72) Inventor: Toru Nakahara, Fujisawa (JP)

(73) Assignee: NSK LTD., Tokyo (JP)

( * ) Notice: Subject to any disclaimer, the term of this patent is extended or adjusted under 35 U.S.C. 154(b) by 0 days.

(21) Appl. No.: 15/538,806

(22) PCT Filed: Dec. 24, 2015

(86) PCT No.: PCT/JP2015/085921
§ 371 (c)(1),
(2) Date: Jun. 22, 2017

(87) PCT Pub. No.: WO2016/104556
PCT Pub. Date: Jun. 30, 2016

(65) Prior Publication Data
US 2017/0348069 A1    Dec. 7, 2017

(30) Foreign Application Priority Data

Dec. 25, 2014 (JP) .................. 2014-262876
Aug. 24, 2015 (JP) .................. 2015-165067

(51) Int. Cl.
*A61C 1/18*      (2006.01)
*F16C 19/06*    (2006.01)
(Continued)

(52) U.S. Cl.
CPC ............... *A61C 1/181* (2013.01); *A61C 1/05* (2013.01); *F16C 33/7823* (2013.01);
(Continued)

(58) Field of Classification Search
CPC .. A61C 1/05; A61C 1/08; A61C 1/181; A61C 3/00; A61C 1/14; A61C 1/057;
(Continued)

(56) References Cited

U.S. PATENT DOCUMENTS 4,249,896 A * 2/1981 Kerfoot, Jr. .............. A61C 1/05
                                                              433/126
4,533,265 A    8/1985 Woodbridge
(Continued)

FOREIGN PATENT DOCUMENTS

CN    102562816 A    7/2012
CN    203285855 U    11/2013
(Continued)

OTHER PUBLICATIONS

Communication dated Nov. 16, 2017, issued by the European Patent Office in counterpart European Patent Application No. 15873124.0.
(Continued)

*Primary Examiner* — Marcus Charles
(74) *Attorney, Agent, or Firm* — Sughrue Mion, PLLC

(57) ABSTRACT

When compressed air does not act, a seal member is in contact with an outer periphery of an inner ring. When the compressed air acts, a contact area between the seal member and the outer periphery of the inner ring is reduced, as compared to when the compressed air does not act. Accordingly, it is possible to provide an air turbine bearing unit capable of promptly stopping rotation.

3 Claims, 14 Drawing Sheets

(51) Int. Cl.
*F16C 19/54* (2006.01)
*A61C 1/05* (2006.01)
*F16C 33/78* (2006.01)
*F16C 41/00* (2006.01)

(52) U.S. Cl.
CPC ........ *F16C 33/7856* (2013.01); *F16C 41/001* (2013.01); *F16C 19/06* (2013.01); *F16C 19/54* (2013.01); *F16C 2316/13* (2013.01)

(58) Field of Classification Search
CPC ........ F16C 19/06; F16C 19/54; F16C 19/305; F16C 35/067; F16C 35/073; F16C 33/32; F16D 15/065
USPC ........ 384/477, 484, 490; 277/349, 353, 402; 433/115, 132
See application file for complete search history.

(56) References Cited

U.S. PATENT DOCUMENTS

| 5,676,542 | A | 10/1997 | Lingenhole et al. |
| 5,779,474 | A * | 7/1998 | Gonser ............ A61C 1/14 433/106 |
| 2004/0018467 | A1 | 1/2004 | Tanaka et al. |
| 2007/0087308 | A1 * | 4/2007 | Flock ............ A61C 1/141 433/132 |
| 2014/0037240 | A1 | 2/2014 | Bussit et al. |

FOREIGN PATENT DOCUMENTS

| DE | 102012000757 | † | 7/2013 | |
| DE | 202014105257 U1 * | 12/2014 | ............ A61C 1/08 |
| DE | 10 2012 000 757 A1 | 10/2016 | |
| EP | 0497139 A1 | 8/1992 | |
| EP | 1208809 A2 * | 5/2002 | ............ A61C 1/05 |
| EP | 2469110 A1 | 6/2012 | |
| JP | 62-194215 U | 12/1987 | |
| JP | 8-66411 A | 3/1996 | |
| JP | 9-151948 A | 6/1997 | |
| JP | 2001-204740 A | 7/2001 | |
| JP | 2003-135486 A | 5/2003 | |
| JP | 2009-2437 A | 1/2009 | |
| JP | 2009-008224 A | 1/2009 | |
| JP | 2011-169399 A | 9/2011 | |
| JP | 2013-253689 A | 12/2013 | |
| SK | 1314-96 A3 | 5/1998 | |
| SK | 279497 B6 | 12/1998 | |

OTHER PUBLICATIONS

International Search Report (PCT/ISA/210 and PCT/ISA/220) dated Feb. 23, 2016 issued by the International Searching Authority in counterpart International Application No. PCT/JP2015/085921.

Written Opinion (PCT/ISA/237) dated Feb. 23, 2016 issued by the International Searching Authority in counterpart International Application No. PCT/JP2015/085921.

Communication dated Jun. 14, 2016, issued by the Japanese Patent Office in counterpart Japanese application No. 2016-516103.

Communication dated Oct. 25, 2016, issued by the Japanese Patent Office in counterpart Japanese application No. 2016-516103.

Communication dated Mar. 22, 2016, issued by the International Searching Authority in counterpart International application No. PCT/JP2015/085921.

Communication issued by the European Patent Office dated Feb. 13, 2018 in counterpart European Patent Application No. 15873124.0.

\* cited by examiner
† cited by third party

SECTIONAL VIEW OF A PART

SECTIONAL VIEW OF B PART

BEARING UNIT FOR AIR TURBINE

CROSS-REFERENCE TO RELATED APPLICATIONS

This application claims priority to and is a national stage entry, under 35 U.S.C. § 371, of international application No. PCT/JP2015/085921, filed Dec. 24, 2015, and claims priority to Japanese Patent Application No. 2014-262876, filed on Dec. 25, 2014, and Japanese Patent Application No. 2015-165067, filed on Aug. 24, 2015, the disclosures of which are incorporated herein by reference in their entireties.

TECHNICAL FIELD

The present invention relates to a bearing unit for an air turbine.

BACKGROUND ART

As shown in FIG. 26, a dental air turbine handpiece 120 includes a grip part 121 and a head part 122 provided at a tip portion of the grip part 121. An operator performs a cutting operation on teeth while gripping the grip part 121, for example.

Conventionally, there has been known a bearing unit 100 for a dental air turbine configuring the head part 122. As shown in FIG. 27, the head part 122 includes a rotary shaft 101 having one end to which a dental treatment tool (not shown) is to be attached, a turbine blade 102 configured to rotate the rotary shaft 101 by compressed air, and a pair of ball bearings 103, 104 configured to rotatably support the rotary shaft 101. The rotary shaft 101, the turbine blade 102 and the pair of ball bearings 103, 104 are disposed in a head housing 105. Outer rings 106, 107 of the pair of ball bearings 103, 104 are supported via rubber rings 108 mounted in annular concave portions 109, 110 of the head housing 105. The outer ring 107 of the lower ball bearing 104 is urged upwardly by a spring washer 111, so that the pair of ball bearings 103, 104 is applied with preload. That is, the pair of ball bearings 103, 104 configured to support the rotary shaft 101 is combined in a face-to-face arrangement and is applied with positive preload by an elastic force of the spring washer 111.

In the dental air turbine handpiece 120, the ultrahigh-speed rotation is implemented by enabling the compressed air to flow against the turbine blade 102 and thus rotating the rotary shaft 101 by the air pressure.

Patent Document 1 discloses a dental or medical air turbine handpiece configured by a head housing having an air supply opening, a rotary shaft rotatably accommodated in the head housing and including a blade configured to receive the supply air from the air supply opening, and ball bearings configured to vertically rotatably support the rotary shaft within the head housing with the air supply opening being interposed therebetween. Herein, a heat resistance mechanical seal is provided at a side of the ball bearing close to the air supply opening.

Therefore, when a pressure of the supply air acts in the air supply opening, i.e., when the blade is rotating, the heat resistance mechanical seal is elastically deformed to contact the ball bearing and shields the pressure. On the other hand, when the pressure of the supply air is not applied, i.e., when the rotation of the blade is stationary, the heat resistance mechanical seal returns to an original state so as to be in non-contact with the ball bearing. Thereby, it is possible to prevent a situation where lubricant oil filled in the ball bearing is leaked by the pressure of the supply air applied into the ball bearing during usage. Further, when the rotation of the blade stops, the heat resistance mechanical seal and the ball bearing are made not to contact each other, so that a frictional resistance between the heat resistance mechanical seal and the blade is removed upon activation of the blade of the rotary shaft and the blade can be thus smoothly activated.

PRIOR ART DOCUMENTS

Patent Documents

Patent Document 1: JP-A-2003-135486

SUMMARY OF THE INVENTION

Problem to be Solved

The air turbine handpiece as described above is configured to rotate at ultrahigh speed during usage. However, when a user stops the handpiece, it is required to promptly stop the handpiece for reducing a treatment time and the like.

The present invention has been made in view of the above situations, and an object of the present invention is to provide an air turbine bearing unit capable of promptly stopping rotation.

Means for Solving the Problems

The object of the present invention is achieved by following configurations.

According to an aspect of the disclosure, a bearing unit for an air turbine comprises:
a turbine blade configured to be rotated by compressed air;
a rotary shaft to which the turbine blade is integrally fixed and to which a tool can be attached; and
a rolling bearing configured to rotatably support the rotary shaft with respect to a housing,
wherein the rolling bearing includes:
an outer ring fixed to the housing;
an inner ring fixed to the rotary shaft;
a plurality of rolling elements arranged to be freely rollable between the outer ring and the inner ring; and
a seal member fixed to an inner periphery of the outer ring and configured to seal a space between the outer ring and the inner ring,
wherein the seal member is in contact with an outer periphery of the inner ring when the compressed air does not act, and
wherein a contact area between the seal member and the outer periphery of the inner ring is reduced when the compressed air acts, as compared to when the compressed air does not act.

The seal member includes a lip part which is capable of contacting the outer periphery of the inner ring and is elastically deformable, and
wherein the lip part is inclined in a supply direction of the compressed air toward a radially inner side.

The seal member includes a lip part which is capable of contacting the outer periphery of the inner ring and is elastically deformable, and wherein the lip part is inclined axially outward from a core or a base part of the seal member toward a radially inner side.

At least a part of the outer periphery of the inner ring, to which the seal member is to contact, is a planar surface.

The inner periphery of the outer ring is formed with a groove portion for fixing therein the seal member, and
wherein a base part of the seal member provided at a radially outer end portion and formed of an elastic material is fixed to the groove portion by a snap ring.

The inner periphery of the outer ring is formed with a groove portion for fixing therein the seal member, and
wherein a base part of the seal member provided at a radially outer end portion and formed of an elastic material is crimped to be fixed to the groove portion.

The inner periphery of the outer ring is formed with a groove portion for fixing therein the seal member, and
wherein a base part of the seal member provided at a radially outer end portion and formed of an elastic material is sandwiched to be fixed by both axial surfaces of the groove portion.

The inner periphery of the outer ring is formed with a groove portion for fixing therein the seal member, and
wherein a base part of the seal member provided at a radially outer end portion and formed of a metal material is crimped to be fixed to the groove portion.

The inner periphery of the outer ring is formed with a groove portion for fixing therein the seal member,
wherein the groove portion includes a tapered surface inclined radially outward toward an axially inner side, and an axially inner surface extending radially inward from an axially inner end portion of the tapered surface, and
wherein a base part of the seal member provided at a radially outer end portion and formed of a metal material contacts the tapered surface and the axially inner surface to be fixed to the groove portion.

The inner ring extends axially outward beyond the outer ring, and
wherein an inner periphery of the seal member is in contact with the outer periphery of the inner ring at an axially outer side than the outer ring.

The compressed air acts, the seal member is in a non-contact state with the outer periphery of the inner ring.

The compressed air does not act, a contact region where an inner periphery of the seal member is in contact with the outer periphery of the inner ring is 10% or greater of an entire inner periphery of the seal member.

The compressed air does not act, a length of a part of the seal member in contact with the outer periphery of the inner ring is 50 µm or greater and 200 µm or less.

Effects of the Invention

According to the bearing unit for an air turbine of the present invention, when the supply of the compressed air is stopped so as to stop an operation, since the compressed air does not act on the seal member, the contact area between the seal member and the outer periphery of the inner ring increases, as compared to when the compressed air acts (during the operation). Therefore, the seal member functions as a brake of the rotary shaft, so that it is possible to promptly stop the rotary shaft.

DESCRIPTION OF EMBODIMENTS

Hereinafter, a bearing unit for an air turbine according to each embodiment of the present invention will be described in detail with reference to the drawings. In the below descriptions, the bearing unit for an air turbine is applied to a dental air turbine handpiece. However, the present invention can also be applied to other utilities, for example a home appliance motor and the like.

(First Embodiment)

Figure 1:
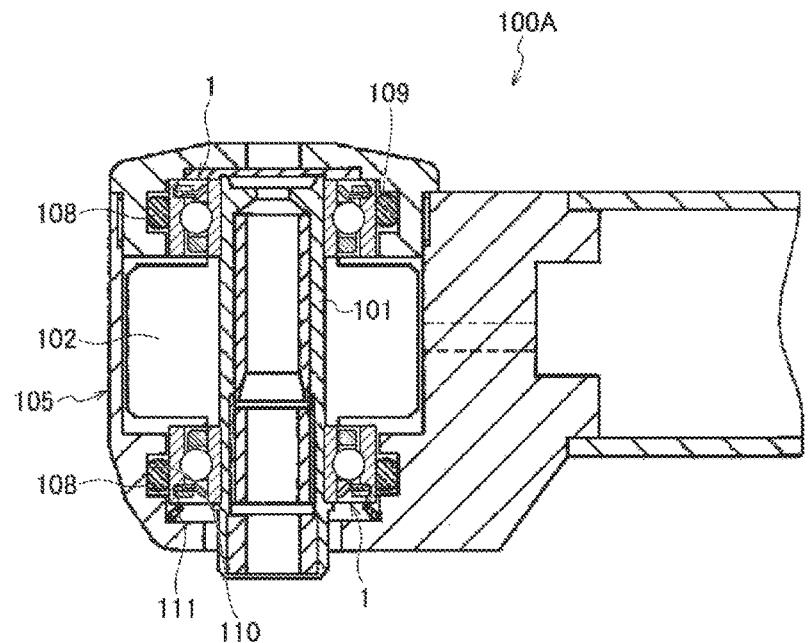
FIG. 1 is a sectional view of main parts of a dental air turbine according to a first embodiment.
Figure 2:
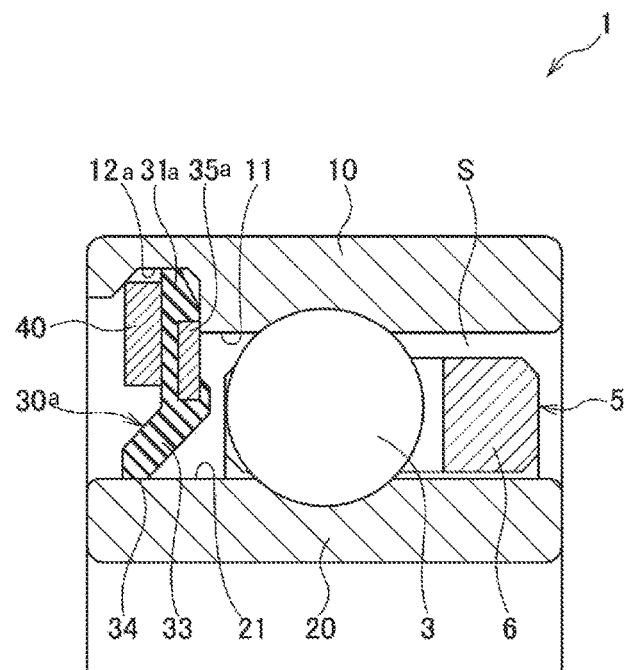
FIG. 2 is a partially sectional view of a rolling bearing according to the first embodiment in a stationary state.
Figure 26:
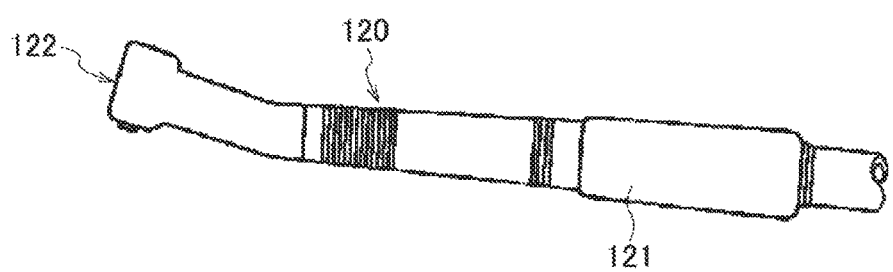
FIG. 26 is a schematic side view of a dental air turbine handpiece.
Figure 27:
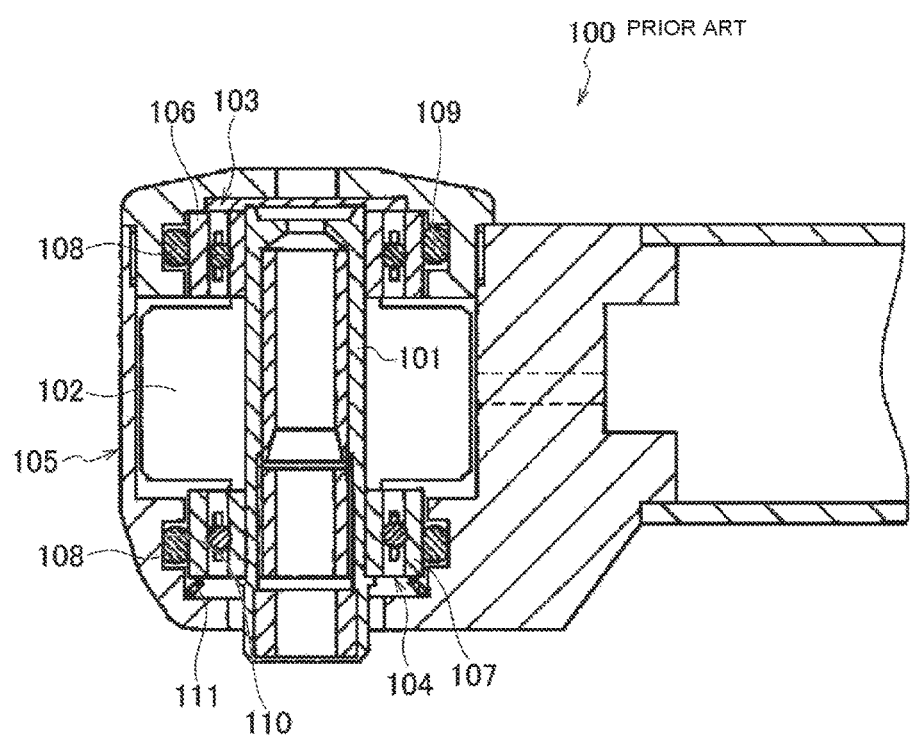
FIG. 27 is a sectional view of main parts of the dental air turbine.

FIG. 1 shows a bearing unit for an air turbine according to a first embodiment, and FIG. 2 shows a rolling bearing 1 configuring the bearing unit for an air turbine according to the first embodiment. As shown in FIG. 1, the bearing unit 100A for an air turbine includes a turbine blade 102 configured to be rotated by compressed air, a rotary shaft 101 to which the turbine blade 102 is integrally fixed and which has one end to which a tool (for example, a dental treatment tool) can be attached, and rolling bearings 1 configured to rotatably support the rotary shaft 101 with respect to a housing 105. In the rolling bearing 1 of FIG. 2, the compressed air is supplied from the right toward the left upon driving of the handpiece. The bearing unit for an air turbine according to the first embodiment is different from the conventional configuration shown in FIG. 26 in the configuration of the rolling bearing 1. Accordingly, the same or equivalent configurations as or to the conventional art, including the turbine blade 102, the rotary shaft 101, the head housing 105 and the like, are denoted with the same reference numerals. It is noted that the bearing unit for an air turbine is not limited to the configuration of FIG. 1.

The rolling bearing 1 includes an outer ring 10 fixed to the housing 105, an inner ring 20 fixed to the rotary shaft 101, a plurality of balls (rolling elements) 3 arranged to be freely rollable between the outer ring 10 and the inner ring 20, and a cage 5 configured to retain each of the plurality of balls 3. The cage 5 is a so-called crown type cage, and a rim part 6 having a substantially circular ring shape is positioned at a upstream side (a right side in FIG. 2) of the ball 3 in a supply direction of the compressed air.

An inner periphery 11 of the outer ring 10 is formed with a groove portion 12 for fixing therein a seal member 30 at a downstream side (a left side in FIG. 2) of the ball 3 in the supply direction of the compressed air. It is noted that the present invention is not limited to the configuration where the seal member 30 is arranged at the downstream side of the ball 3 in the supply direction of the compressed air as long as a brake function (described later) is realized. For example, the seal member 30 may be arranged at the upstream side (the right side in FIG. 2) of the ball 3 in the supply direction of the compressed air or a pair of the seal members may be arranged at both downstream and upstream sides of the ball 3 in the supply direction of the compressed air.

The seal member 30 includes a base part 31 which extends radially and made of an elastic material and a lip part 33 integrally formed with the base part 31 and made of an elastic material. The base part 31 is configured to enclose a core 35 at a radially inner side thereof, so that the shape and strength thereof are ensured. Also, the base part 31 is inserted and fixed to the groove portion 12 with being in contact with a snap ring 40. In the first embodiment, a C-shaped snap ring is used as the snap ring 40 for easy attachment. However, a circular ring-shaped snap ring or the like may also be used. When the compressed air flows against the seal member 30, the seal member 30 is strongly fixed to the outer ring 10 by a frictional force between the metallic snap ring 40 and the base part 31.

Figure 4:
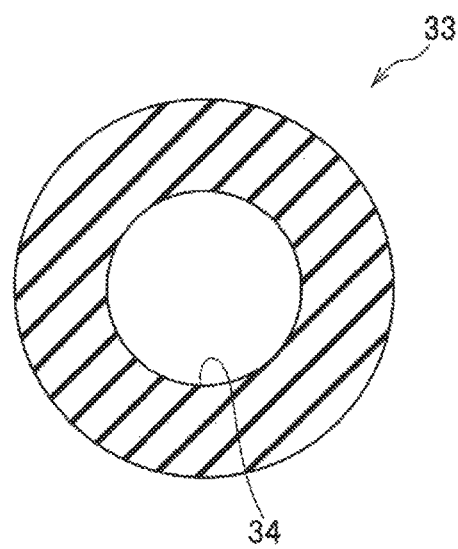
FIG. 4 is a sectional view of a lip part.

The lip part 33 has a substantially circular ring shape inclined in the supply direction of the compressed air (a direction from the right toward the left in FIG. 2) toward a radially inner side and is configured to be contactable to an outer periphery 21 of the inner ring 20. That is, the lip part 33 is inclined axially outward from the core 35 toward the radially inner side. Referring to a sectional view of FIG. 4, an inner periphery 34 of the lip part 33 has a substantially circular ring shape (a section is a substantial circle shape), i.e., a seal inner diameter is a substantially circular ring shape. At least a part of an outer periphery 21 of the inner ring 20, to which the lip part 33 is to contact, has a planar surface shape (a substantially circular ring shape). Therefore, the inner periphery 34 of the lip part 33, which is the seal inner diameter, can contact the outer periphery 21 of the inner ring 20 over a substantial 100% area of the entire area thereof, i.e., a substantially complete contact can be made. Accordingly, the seal member 30 is configured to seal a bearing inner space S between the inner periphery 11 of the outer ring 10 and the outer periphery 21 of the inner ring 20.

Figure 3:
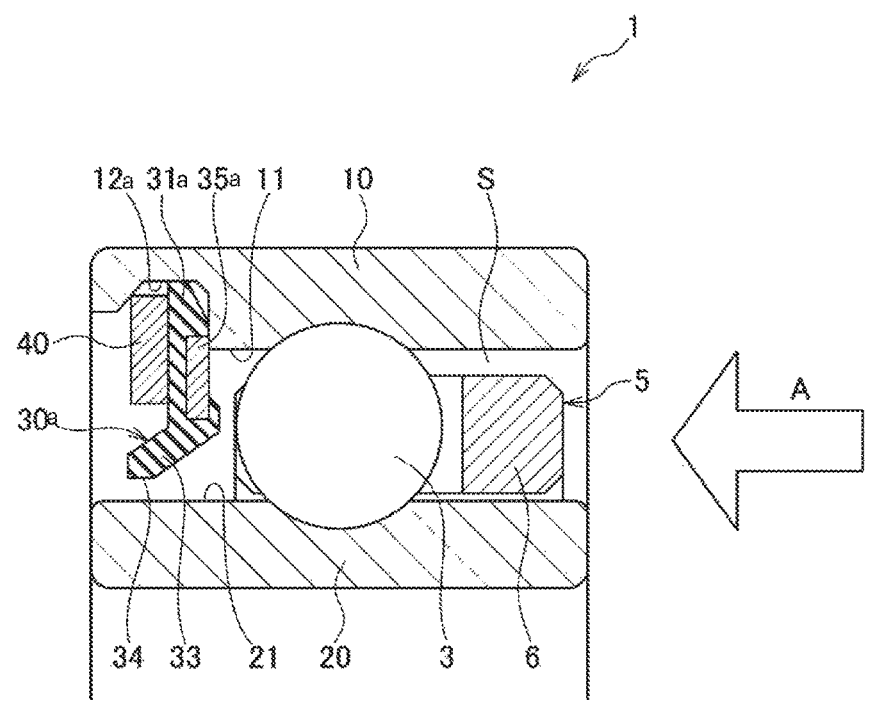
FIG. 3 is a partially sectional view of the rolling bearing according to the first embodiment in an operating state.
Figure 5:
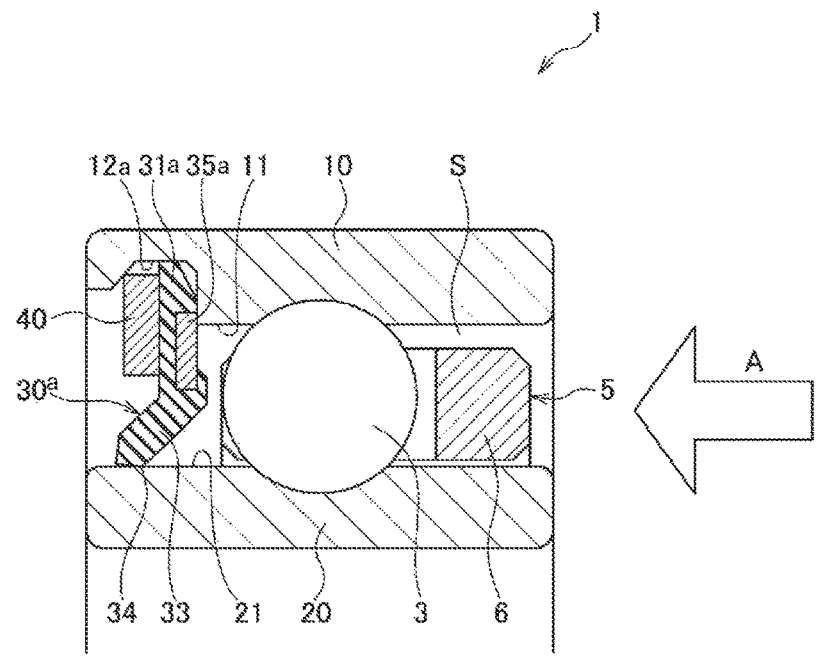
FIG. 5 is a partially sectional view of a rolling bearing according to a modified embodiment of the first embodiment in the operating state.

Herein, when the compressed air is supplied to the turbine blade so as to drive the dental air turbine handpiece, the compressed air flows into the bearing inner space S from the right toward the left, as shown with an arrow A in FIG. 3. The compressed air acts on the seal member 30, thereby elastically deforming the lip part 33 toward the left. Therefore, when the compressed air acts, a contact area between the inner periphery 34 of the lip part 33 and the outer periphery 21 of the inner ring 20 is reduced, as compared to when the compressed air does not act. In the example of FIG. 3, the inner periphery 34 of the lip part 33 and the outer periphery 21 of the inner ring 20 are in non-contact with each other and the contact area is zero. That is, the lip part 33 is in an open state. As shown in an example of FIG. 5, a configuration may be employed in which when the compressed air acts, the inner periphery 34 of the lip part 33 and the outer periphery 21 of the inner ring 20 are kept in contact with each other and the contact area between the inner periphery 34 of the lip part 33 and the outer periphery 21 of the inner ring 20 is reduced, as compared to when the compressed air does not act.

On the other hand, when the supply of the compressed air is stopped so as to stop the dental air turbine handpiece, since the compressed air does not act on the lip part 33, the lip part 33 returns to the state of FIG. 2, the inner periphery 34 of the lip part 33 and the outer periphery 21 of the inner ring 20 are in contact with each other, and the contact area with the outer periphery 21 of the inner ring 20 increases. That is, the lip part 33 is in a close state. Therefore, the lip part 33 functions as a brake of the inner ring 20 and the rotary shaft 101 to which the inner ring 20 is fixed, so that it is possible to promptly stop the rotary shaft 101.

In the meantime, as described above, since the lip part 33 has an inclined shape so as to be easily elastically deformable by the action of the compressed air, it is possible to open and close the lip part 33 with good sensitivity by the compressed air.

Since at least the part, of the outer periphery 21 of the inner ring 20, to which the inner periphery 34 of the lip part 33 is to contact, is a planar surface (a substantially circular ring shape), it is possible to increase the contact area between the outer periphery 21 of the inner ring 20 and the inner periphery 34 of the lip part 33, so that it is possible to improve the brake function of the lip part 33. Particularly, in the first embodiment, the inner periphery 34 of the lip part 33 has the substantially circular ring shape, which is similar to the shape of the outer periphery 21 of the inner ring 20. Therefore, since the inner periphery 34 of the lip part 33 contacts the outer periphery 21 of the inner ring 20 over a substantial 100% of the entire area thereof, it is possible to further improve the brake function of the lip part 33.

Also, the inner periphery 11 of the outer ring 10 is formed with the groove portion 12 for fixing therein the seal member 30, and the base part 31 of the seal member 30 provided at the radially outer end portion and formed of the elastic material is fixed to the groove portion 12 by the snap ring 40. Therefore, since the seal member 30 is strongly fixed to the outer ring 10, it is possible to prevent the seal member 30 from being separated when the compressed air is applied.

(Second Embodiment)

Figure 6:
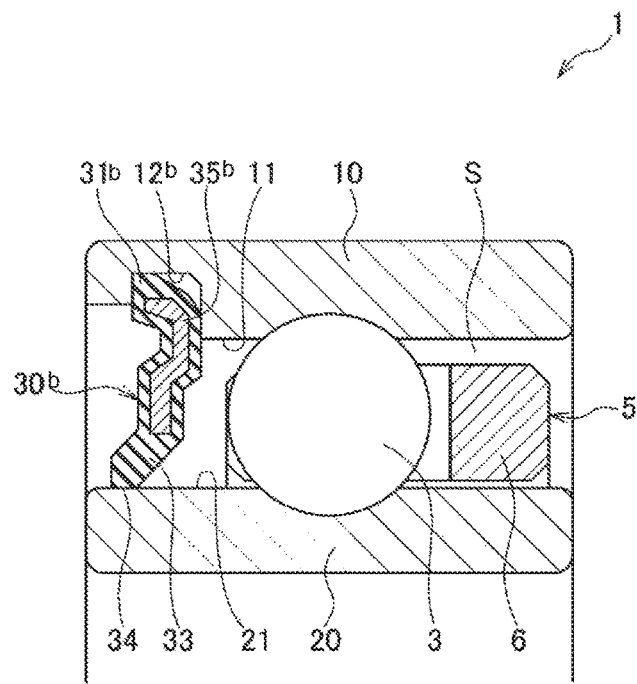
FIG. 6 is a partially sectional view of a rolling bearing according to a second embodiment in the stationary state.
Figure 7:
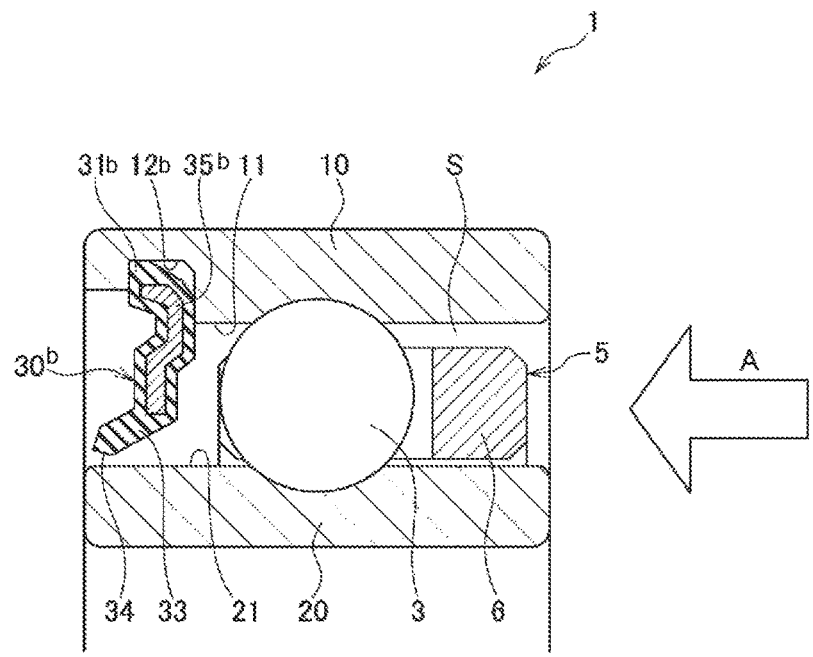
FIG. 7 is a partially sectional view of the rolling bearing according to the second embodiment in the operating state.

A second embodiment is different from the first embodiment in the manner of fixing the seal member 30 to the outer ring 10. As shown in FIG. 6 and FIG. 7, the base part 31 of the seal member 30 is configured to enclose the core 35 as a whole, so that the shape and strength are ensured. The lip part 33 is inclined axially outward from the core 35 toward the radially inner side. A radially outer end portion of the base part 31 is crimped to be fixed to the groove portion 12 of the outer ring 10. In this manner also, since the seal member 30 is strongly fixed to the outer ring 10, it is possible to prevent the seal member 30 from being separated when the compressed air is applied. The other configurations and effects are the same as the first embodiment.

Figure 8:
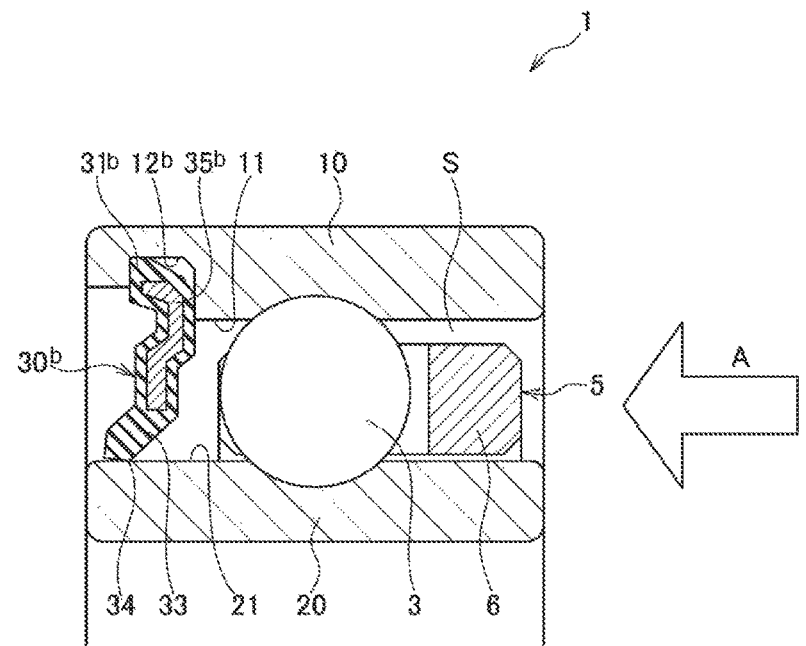
FIG. 8 is a partially sectional view of a rolling bearing according to a modified embodiment of the first embodiment in the operating state.

Also in the second embodiment, when the compressed air acts, the contact area between the inner periphery 34 of the lip part 33 and the outer periphery 21 of the inner ring 20 is reduced, as compared to when the compressed air does not act. That is, the inner periphery 34 of the lip part 33 and the outer periphery 21 of the inner ring 20 may be in non-contact with each other (the contact area is zero). Alternatively, as shown in an example of FIG. 8, a configuration may be also employed in which the inner periphery 34 of the lip part 33 and the outer periphery 21 of the inner ring 20 are kept in contact with each other and the contact area is reduced, as compared to when the compressed air does not act.

(Third Embodiment)

Figure 9:
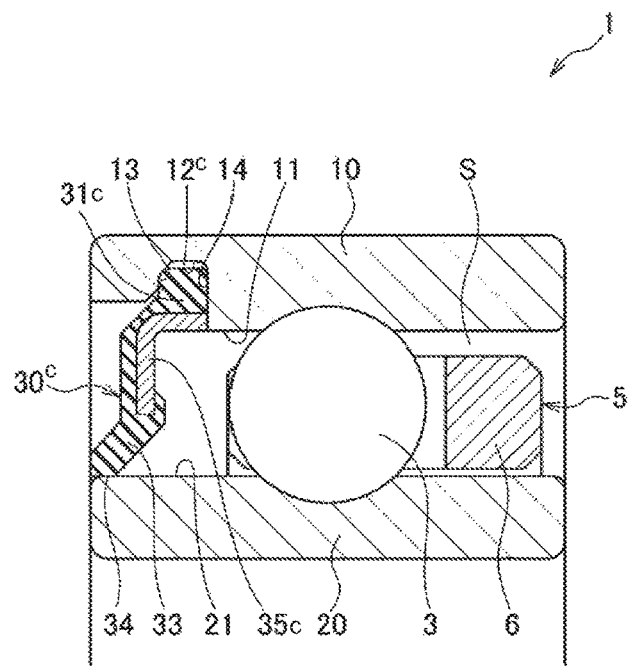
FIG. 9 is a partially sectional view of a rolling bearing according to a third embodiment in the stationary state.

A third embodiment is different from the above embodiments in the manner of fixing the seal member 30 to the outer ring 10. As shown in FIG. 9, the base part 31 of the seal member 30 is configured to enclose an outer side of a cylindrical part of the core 35 having an L-shaped section, so that the shape and strength thereof are ensured. The lip part 33 is inclined axially outward from the core 35 toward the radially inner side. The radially outer end portion of the base part 31 is axially sandwiched to be fixed by both axial surfaces 13, 14 of the groove portion 12 of the outer ring 10. In this manner also, since the seal member 30 is strongly fixed to the outer ring 10, it is possible to prevent the seal member 30 from being separated when the compressed air is applied. The other configurations and effects are the same as the above embodiments.

Also in the third embodiment, when the compressed air acts, the contact area between the inner periphery 34 of the lip part 33 and the outer periphery 21 of the inner ring 20 is reduced, as compared to when the compressed air does not act. That is, the inner periphery 34 of the lip part 33 and the outer periphery 21 of the inner ring 20 may be in non-contact with each other (the contact area is zero). Alternatively, a configuration may be also employed in which the inner periphery 34 of the lip part 33 and the outer periphery 21 of the inner ring 20 are kept in contact with each other and the contact area is reduced, as compared to when the compressed air does not act.

(Fourth Embodiment)

Figure 10:
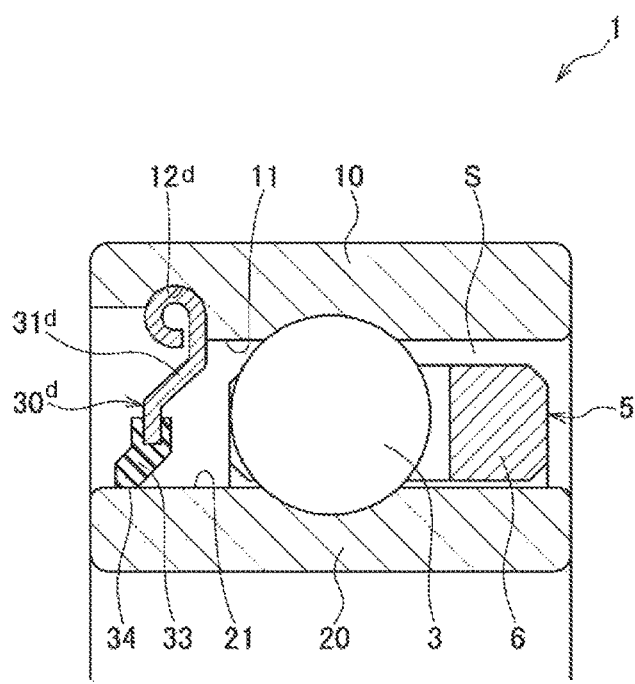
FIG. 10 is a partially sectional view of a rolling bearing according to a fourth embodiment in the stationary state.

A fourth embodiment is different from the above embodiments in the manner of fixing the seal member 30 to the outer ring 10. As shown in FIG. 10, the seal member 30 includes the lip part 33 and the base part 31 having a radially inner end portion enclosed by the lip part 33 and made of a metal material extending radially outward from the lip part 33. The lip part 33 is inclined axially outward from the base part 31 toward the radially inner side. That is, in the fourth embodiment, the base part 31 is not enclosed by the elastic material and the metal material thereof is exposed. The radially outer end portion of the base part 31 is crimped to be fixed to the groove portion 12 of the outer ring 10. In this manner also, since the seal member 30 is strongly fixed to the outer ring 10, it is possible to prevent the seal member 30 from being separated when the compressed air is applied. The other configurations and effects are the same as the above embodiments.

Also in the fourth embodiment, when the compressed air acts, the contact area between the inner periphery 34 of the lip part 33 and the outer periphery 21 of the inner ring 20 is reduced, as compared to when the compressed air does not act. That is, the inner periphery 34 of the lip part 33 and the outer periphery 21 of the inner ring 20 may be in non-contact with each other (the contact area is zero). Alternatively, a configuration may be also employed in which the inner periphery 34 of the lip part 33 and the outer periphery 21 of the inner ring 20 are kept in contact with each other and the contact area is reduced, as compared to when the compressed air does not act.

(Fifth Embodiment)

Figure 11:
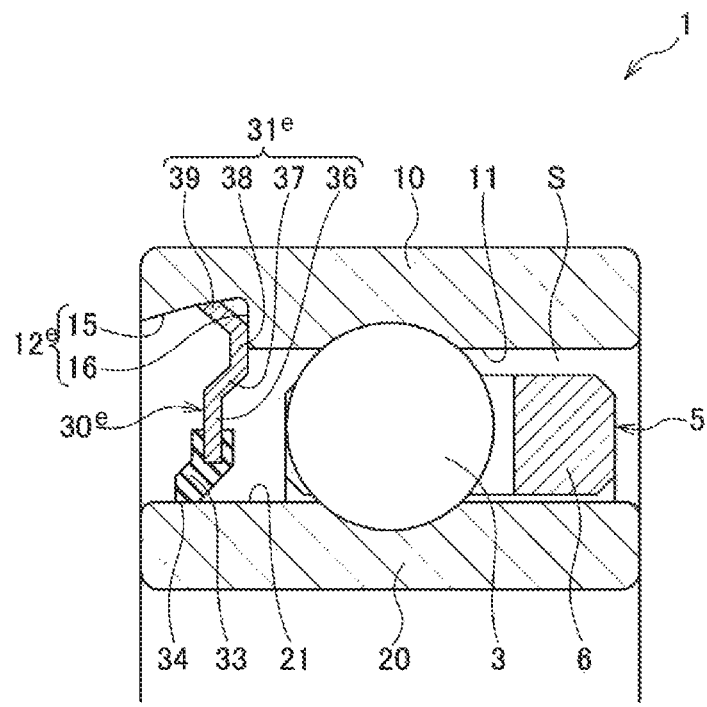
FIG. 11 is a partially sectional view of a rolling bearing according to a fifth embodiment in the stationary state.

A fifth embodiment is different from the above embodiments in the manner of fixing the seal member 30 to the outer ring 10. As shown in FIG. 11, the groove portion 12 of the outer ring 10 has a tapered surface 15 inclined radially outward toward the axially inner side (the side of the balls 3) and an axially inner surface 16 extending radially inward from an axially inner end portion of the tapered surface 15.

The seal member 30 includes the lip part 33 and the base part 31 having a radially inner end portion enclosed by the lip part 33 and made of a metal material extending radially outward from the lip part 33. The lip part 33 is inclined axially outward from the base part 31 toward the radially inner side. That is, in the fifth embodiment, the base part 31 is not enclosed by the elastic material and the metal material thereof is exposed. The base part 31 includes a first extension portion 36 extending radially outward from the lip part 33, a first inclined portion 37 extending with being inclined radially outward and axially inward from the first extension portion 36, a second extension portion 38 extending radially outward from the first inclined portion 37, and a second inclined portion 39 extending with being inclined radially outward and axially outward from the second extension portion 38.

An axially inner surface of the second extension portion 38 contacts the axially inner surface 16 of the groove portion 12 and an outer periphery of the second inclined portion 39 contacts the tapered surface 15 of the groove portion 12, so that the base part 31 is fixed to the groove portion 12. In this manner also, since the seal member 30 is strongly fixed to the outer ring 10, it is possible to prevent the seal member 30 from being separated when the compressed air is applied. The other configurations and effects are the same as the above embodiments.

Also in the fifth embodiment, when the compressed air acts, the contact area between the inner periphery 34 of the lip part 33 and the outer periphery 21 of the inner ring 20 is reduced, as compared to when the compressed air does not act. That is, the inner periphery 34 of the lip part 33 and the outer periphery 21 of the inner ring 20 may be in non-contact with each other (the contact area is zero). Alternatively, a configuration may be also employed in which the inner periphery 34 of the lip part 33 and the outer periphery 21 of the inner ring 20 are kept in contact with each other and the contact area is reduced, as compared to when the compressed air does not act.

The present invention is not limited to the above embodiments, and can be appropriately changed and modified.

Figure 12:
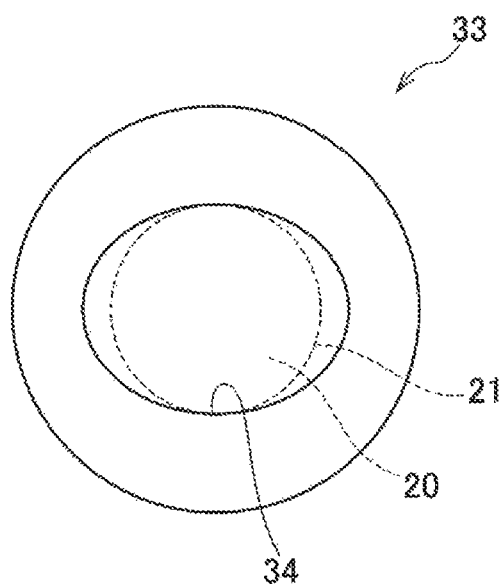
FIG. 12 is a front view of a seal member according to a modified embodiment.
Figure 13:
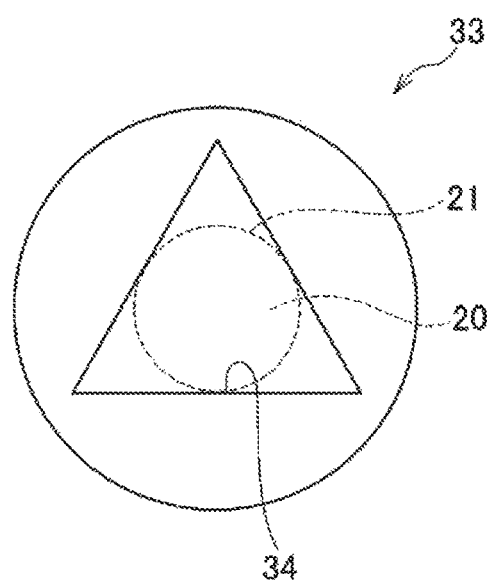
FIG. 13 is a front view of the seal member according to a modified embodiment.
Figure 14:
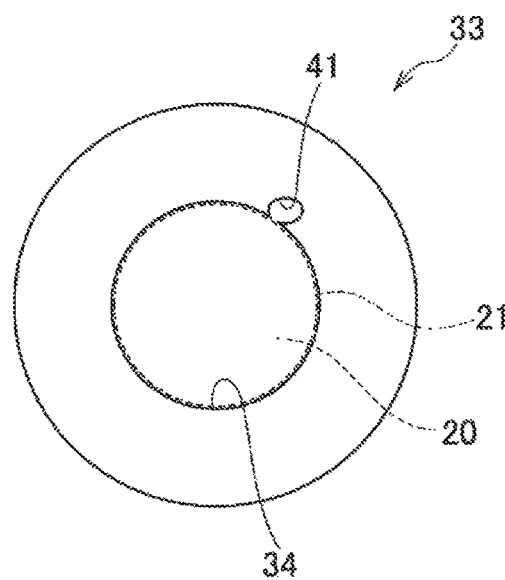
FIG. 14 is a front view of the seal member according to a modified embodiment.
Figure 15:
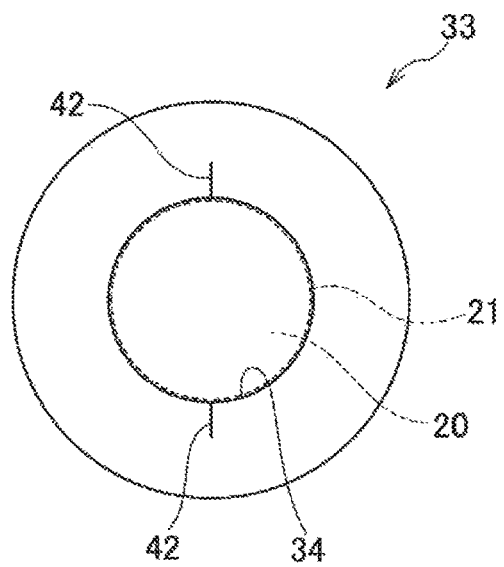
FIG. 15 is a front view of the seal member according to a modified embodiment.
Figure 16:
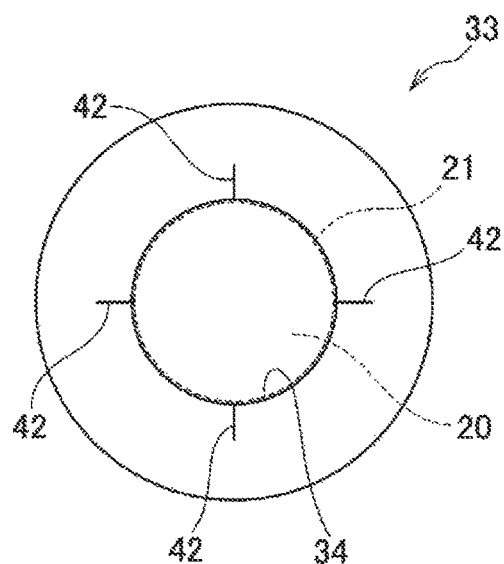
FIG. 16 is a front view of the seal member according to a modified embodiment.
Figure 17:
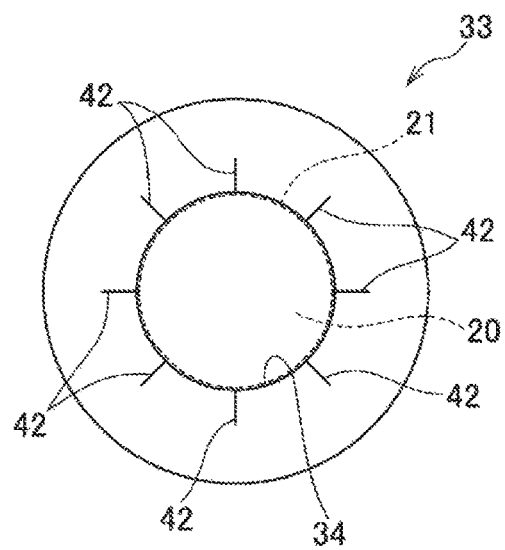
FIG. 17 is a front view of the seal member according to a modified embodiment.

For example, modified embodiments where the inner periphery 34 of the lip part 33, which is the inner diameter of the seal member 30, is formed to have a substantially elliptical section (refer to FIG. 12) or a substantially triangular shape (refer to FIG. 13) without changing the outer diameter shape of the seal member 30 are also within the scope of the present invention. Also, the inner periphery 34 of the lip part 33 may be provided with at least one air hole 41, as shown in FIG. 14, and may be provided with at least one slit 42, as shown in FIGS. 15 to 17. Incidentally, in FIG. 14, an example where one circular air hole 41 is provided is shown. However, two or more air holes 41 may be provided and the shape of the air hole 41 is not limited to the circular shape. Also, in FIGS. 15 to 17, examples are shown in which two, four and eight slits 42 are provided at circumferentially equal intervals, respectively. However, the number and circumferential intervals of the slits 42 are not limited thereto.

Figure 18:
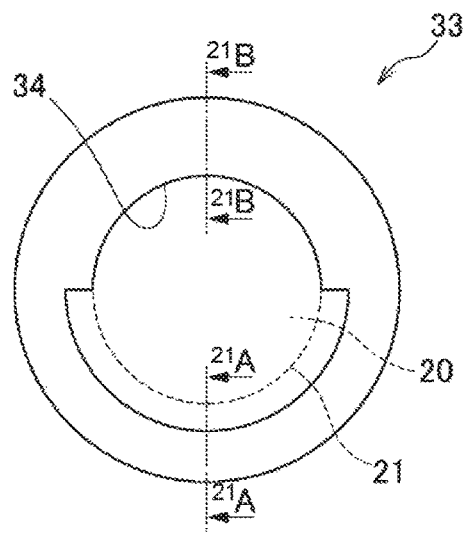
FIG. 18 is a front view of the seal member according to a modified embodiment.
Figure 19:
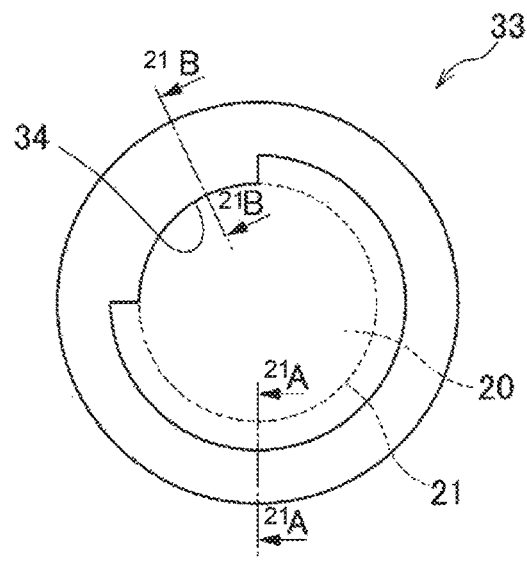
FIG. 19 is a front view of the seal member according to a modified embodiment.
Figure 20:
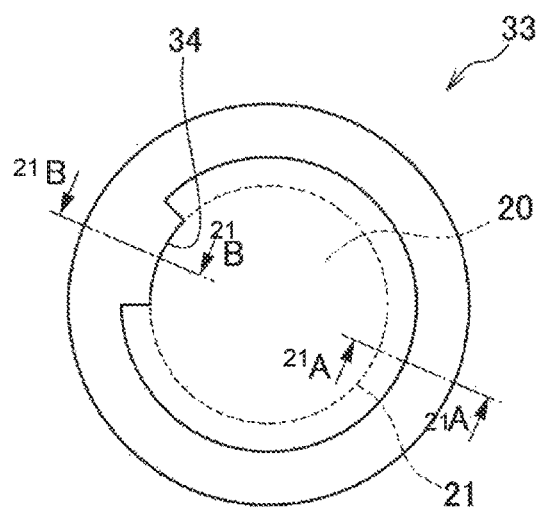
FIG. 20 is a front view of the seal member according to a modified embodiment.

Also, as shown in FIGS. 18 to 20, the tip portion of the lip part 33 may be continuously cut in a circumferential direction, so that the inner periphery 34 of the lip part 33 may partially contact the outer periphery 21 of the inner ring 20. In FIGS. 18 to 20, a contact region (arc length) in which the inner periphery 34 of the lip part 33 is in contact with the outer periphery 21 of the inner ring 20 is 50%, 25% and 10% of the entire inner periphery 34, respectively.

Figure 21A:
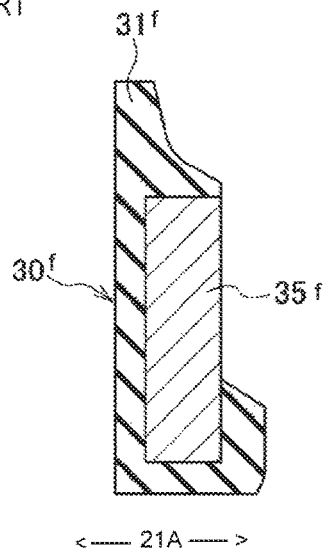
FIG. 21A is a sectional view taken along a 21A-21A line of FIG. 18 to FIG. 20.
Figure 21B:
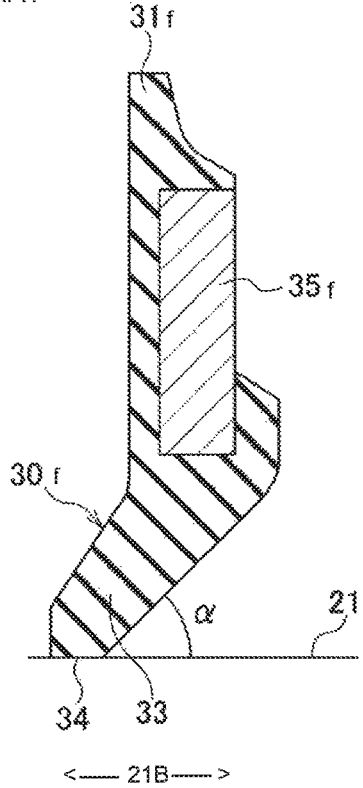
FIG. 21B is a sectional view taken along a 21B-21B line of FIG. 18 to FIG. 20.

In the meantime, FIG. 21A is a sectional view taken along a 21A-21A line of FIG. 18 to FIG. 20, and FIG. 21B is a sectional view taken along a 21B-21B line of FIG. 18 to FIG. 20.

When the compressed air acts, it is preferable that the inner periphery 34 of the lip part 33 be not completely in contact with the outer periphery 21 of the inner ring 20. However, when the seal member 30 is changed from the contact state to the non-contact state, a frictional force is generated between the seal member and the outer periphery 21 of the inner ring 20, so that the state change may not be smoothly made. Therefore, when the inner periphery 34 of the lip part 33 is provided with the air hole 41 or the slits 42, or when the inner periphery 34 of the lip part 33 locally contacts the outer periphery 21 of the inner ring 20, the compressed air can easily pass through the seal member 30, so that it is possible to promote the change from the contact state to the non-contact state. In this way, when the shape of the inner periphery 34 of the lip part 33 is changed, it is possible to appropriately change the contact area between the inner periphery 34 and the outer periphery 21 of the inner ring 20, thereby satisfying the desired brake performance or sealing performance of the lip part 33.

Meanwhile, in order to obtain the brake function, the contact region (the arc length, in the examples of FIGS. 18 to 20) of the inner periphery 34 of the lip part 33 shown in FIG. 12 to FIG. 20 Which contacts the outer periphery 21 of the inner ring 20 is over 10% or greater of the entire inner periphery when the compressed air does not act. This is to ease the state change of the seal member 30 from the contact state to the non-contact state when the compressed air flows against the seal member 30. When the contact region is equal to or less than 10% of the entire inner periphery, the contact area between the inner periphery 34 of the lip part 33 and the outer periphery 21 of the inner ring 20 is small when the compressed air does not act, so that the brake function may not be sufficiently obtained.

In the meantime, in a case where an axial width of the inner periphery 34 of the lip part 33 in contact with the inner ring 20 is uniform over a circumferential direction, the contact area of the inner periphery 34 of the lip part 33 is preferably 10% or greater of the entire area of the inner periphery When the compressed air does not act.

Figure 22:
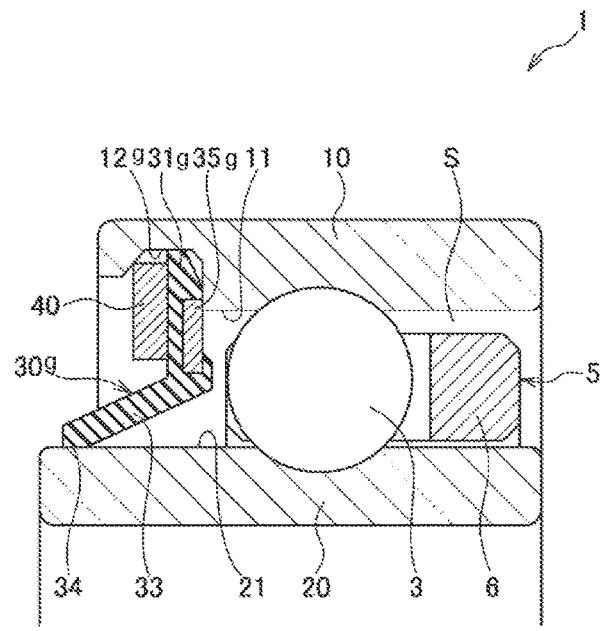
FIG. 22 is a partially sectional view of a rolling bearing according to another modified embodiment.

Further, the inner ring 20 may extend axially outward beyond the outer ring 10 and the seal member 30 may extend axially outward beyond the outer ring 10 as long as the sealing performance is secured, as shown in FIG. 22. In this case, the inner periphery 34 of the lip part 33 of the seal member 30 is in contact with the outer periphery 21 of the inner ring 20 at an axially outer side than the outer ring 10. According to this configuration, since it is possible to largely incline the lip part 33, it is possible to open and close the lip part 33 more easily by the compressed air.

Figure 23:
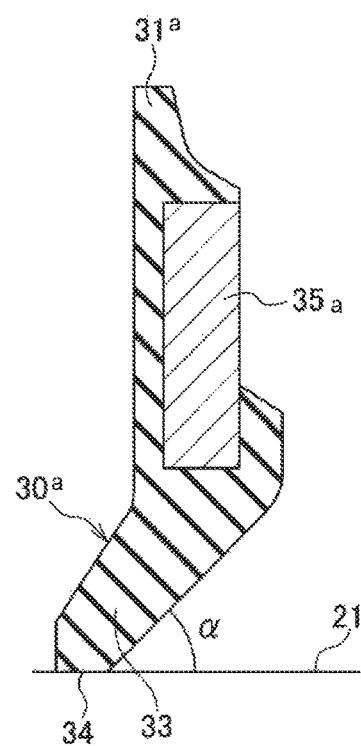
FIG. 23 is a sectional view for illustrating a contact angle of the seal member shown in FIG. 1.

Further, as shown in FIG. 23, the lip part 33 preferably contacts the outer periphery 21 of the inner ring 20 with an inclined angle α of the lip part 33 of the seal member 30 being set to 35° to 55°. Thereby, when the compressed air acts, the air efficiently acts on the lip part 33 to smoothly open the seal member 30, so that it is possible to implement the high-speed rotation with the low air pressure.

When the compressed air does not act, the lip part 33 of the seal member 30 contacts the outer periphery 21 of the inner ring 20, but in a case where a length of the contact part of the seal member 30 with the outer periphery 21 of the inner ring 20 is less than 50 μm, the brake function is weakened, so that it takes time to stop the turbine. On the other hand, when the length is greater than 200 μm, the elastic deformation is difficult to occur upon the action of the compressed air, so that it is difficult to make the contact area small. Therefore, the length is preferably set to 50 μm or greater and 200 μm or less.

EXAMPLES

Herein, in order to confirm the effects of the present invention, evaluation tests were performed using a plurality of rolling bearings having different seal members. Specifically, the turbine was rotated at states described later by the air pressure and the time at which the turbine shaft was completely stopped when stopping the air pressure of the turbine was checked.

In each bearing unit used for those tests, a pair of rolling bearings were configured as follows. The tests were performed without changing the other turbine specification, the air pressure condition and the like.

Figure 24:
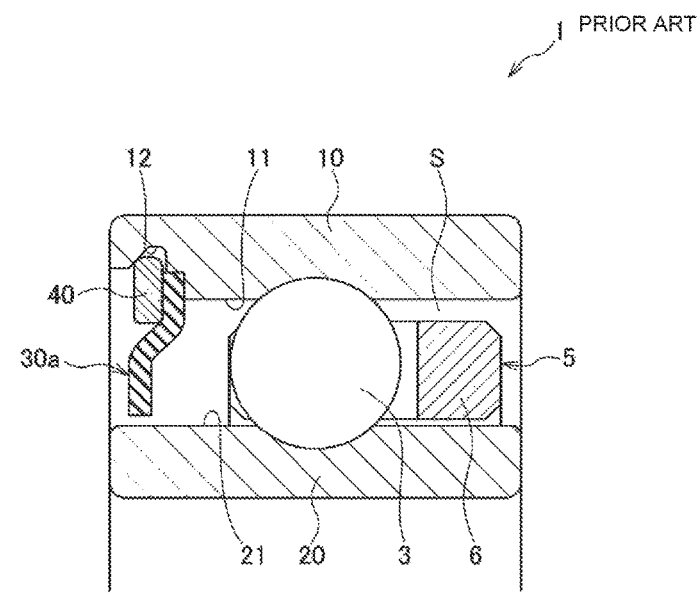
FIG. 24 is a partially sectional view of a rolling bearing of the conventional art.

Test Example 1:

The rolling bearings having a non-contact seal 30a shown in FIG. 24 were employed as both the rolling bearings.

Test Example 2:

The rolling bearing (FIG. 2) including the seal member 30 in which the lip part 33 is not provided with a slit (FIG. 4) was employed as one rolling bearing, and the rolling bearing shown in FIG. 24 was employed as the other rolling bearing.

Test Example 3:

The rolling bearing (FIG. 2) including the seal member 30 in which the lip part 33 is provided with the two slits 42 (FIG. 15) was employed as one rolling bearing, and the rolling bearing shown in FIG. 24 was employed as the other rolling bearing.

Test Example 4:

The rolling bearing (FIG. 2) including the seal member 30 in which the lip part 33 is provided with the four slits 42

(FIG. 16) was employed as one rolling bearing, and the rolling bearing shown in FIG. 24 was employed as the other rolling bearing.

Test Example 5:

The rolling bearing (FIG. 2) including the seal member 30 in which the lip part 33 is provided with the eight slits (FIG. 17) was employed as one rolling bearing, and the rolling bearing shown in FIG. 24 was employed as the other rolling bearing.

Test Example 6:

The rolling bearing (FIG. 2) including the seal member 30 in which the lip part 33 contacts the outer periphery 21 of the inner ring 20 over the 50% region (FIG. 18) was employed as one rolling hearing, and the rolling hearing shown in FIG. 24 was employed as the other rolling bearing.

Test Example 7:

The rolling bearing (FIG. 2) including the seal member 30 in which the lip part 33 contacts the outer periphery 21 of the inner ring 20 over the 25% region (FIG. 19) was employed as one rolling bearing, and the rolling bearing shown in FIG. 24 was employed as the other rolling bearing.

Test Example 8:

The rolling bearing (FIG. 2) including the seal member 30 in which the lip part 33 contacts the outer periphery 21 of the inner ring 20 over the 15% region (FIG. 20) was employed as one rolling bearing, and the rolling bearing shown in FIG. 24 was employed as the other rolling bearing.

Figure 25:
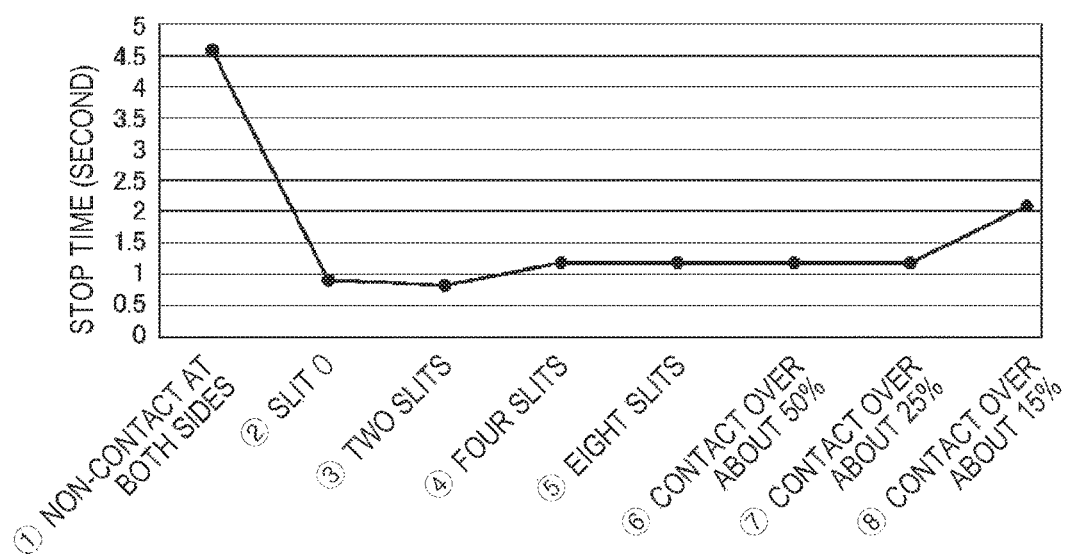
FIG. 25 shows a relation between a sectional shape of a lip part and stop time.

As can be seen from a graph of FIG. 25, in Test Example 1, the stop time of the turbine was about 4.5 seconds. However, in Test Examples 2 to 8 where the rolling bearing of the present invention was employed as one rolling bearing, the stop time was all about 2 seconds or less. That is, it is possible to confirm the effects of the present invention. Also, even when the slits are provided or when the contact region is 15% or greater of the inner periphery, as in Test Examples 3 to 8, the stop time was about 2 seconds or less. Therefore, it is possible to increase the number of rotations of the turbine by changing the contact region of the seal and to use the seal depending on the performances of the turbine.

Further, in Test Examples 2 to 8, the seal members in which the inclined angle a (refer to FIG. 23) of the lip part 33 of the seal member 30 is within the tolerance range of 45°±10° (i.e., 35° to 55°) were employed. Thereby, it is possible to confirm that the seal member 30 is smoothly opened when the compressed air acts.

Further, in Test Examples 2 to 8, the seal members having the length of 50 μm or greater and 200 μm or less were employed. Thereby, it is possible to confirm that the stop time can be shortened.

The present application is based on a Japanese Patent Application No. 2014-262876 filed on Dec. 25, 2014 and a Japanese Patent Application No. 2015-165067 filed on Aug. 24, 2015, the contents of which are herein incorporated for reference.

DESCRIPTION OF REFERENCE NUMERALS

1: rolling bearing
3: ball (rolling element)
5: holder
6: rim part
10: outer ring
11: inner periphery
12 (shown as 12a, 12b, 12c, 12d, 12e, 12f, and 12g, according to various embodiments): groove portion
13, 14: both axial surfaces
15: tapered surface
16: axially inner surface
20: inner ring
21: outer periphery
30 (shown as 30a, 30b, 30c, 30d, 30e, 30f, and 30g, according to various embodiments): seal member
31 (shown as 31a, 31b, 31c, 31d, 31e, 31f, and 31g, according to various embodiments): base part
33: lip part
34: inner periphery
35 (shown as 35a, 35b, 35c, 35d, 35e, 35f, and 35g, according to various embodiments): core
36: first extension portion
37: first inclined portion
38: second extension portion
39: second inclined portion
40: snap ring
41: air hole
42: slit
100A: bearing unit for an air turbine
S: bearing inner space

The invention claimed is:

1. A bearing unit, comprising:
a turbine blade configured to be rotated by compressed air;
a rotary shaft to which the turbine blade is integrally fixed and to which a tool can be attached; and
a rolling bearing configured to rotatably support the rotary shaft with respect to a housing,
wherein the rolling bearing includes:
an outer ring fixed to the housing;
an inner ring fixed to the rotary shaft;
a plurality of rolling elements arranged to be freely rollable between the outer ring and the inner ring; and
a seal member fixed to an inner periphery of the outer ring and configured to seal a space between the outer ring and the inner ring,
wherein the seal member includes a base part which extends radially and a lip part which is elastically deformable and extends from a radially inner end of the base part and inclined in a supply direction of the compressed air toward a radially inner side, the lip part being deformed by the compressed air,
wherein an inner periphery of the lip part of the seal member is in contact with an outer periphery of the inner ring when the compressed air does not deform the lip part, and
wherein a contact area between the seal member and the outer periphery of the inner ring is reduced when the compressed air deforms the lip part, as compared to when the compressed air does not deform the lip part.

2. The bearing unit according to claim 1,
wherein when the compressed air deforms the lip part, the seal member is in a non-contact state with the outer periphery of the inner ring.

3. A dental air turbine hand piece comprising the bearing unit according to claim 1.

* * * * *